(12) United States Patent
Alexander et al.

(10) Patent No.: US 11,869,379 B2
(45) Date of Patent: Jan. 9, 2024

(54) ABDOMINAL HERNIA SIMULATION MODEL FOR SURGICAL TRAINING

(71) Applicant: Intuitive Surgical Operations, Inc., Sunnyvale, CA (US)

(72) Inventors: John Alexander, Sunnyvale, CA (US); W. Andrew Grubbs, Chapel Hill, NC (US); Kaity Yu Emerson, Sunnyvale, CA (US); Morgan Dominice Moore, Sunnyvale, CA (US); Megan Harrison Dew, Sunnyvale, CA (US); Samuel David Drew, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 632 days.

(21) Appl. No.: 16/977,861

(22) PCT Filed: Mar. 11, 2019

(86) PCT No.: PCT/US2019/021657
§ 371 (c)(1),
(2) Date: Sep. 3, 2020

(87) PCT Pub. No.: WO2019/177993
PCT Pub. Date: Sep. 19, 2019

(65) Prior Publication Data
US 2021/0043114 A1 Feb. 11, 2021

Related U.S. Application Data

(60) Provisional application No. 62/641,618, filed on Mar. 12, 2018.

(51) Int. Cl.
*G09B 23/30* (2006.01)
*G09B 23/34* (2006.01)
(Continued)

(52) U.S. Cl.
CPC ........... *G09B 23/306* (2013.01); *G09B 23/34* (2013.01); *A61B 18/1482* (2013.01); *A61B 34/30* (2016.02); *A61G 13/04* (2013.01); *A61G 13/06* (2013.01)

(58) Field of Classification Search
CPC ...... G09B 23/30; G09B 23/306; G09B 23/34; A61B 34/30; A61B 18/1482; A61G 13/04; A61G 13/06
See application file for complete search history.

(56) References Cited

U.S. PATENT DOCUMENTS 5,908,302 A 6/1999 Goldfarb
6,474,993 B1 11/2002 Grund et al.
(Continued)

FOREIGN PATENT DOCUMENTS

JP 2018165325 A 10/2018
WO 2017155678 A1 9/2017

OTHER PUBLICATIONS

International Search Report and Written Opinion issued in counterpart PCT Application No. PCT/US2019/021657 dated Jul. 8, 2019 (eight (8) pages).
(Continued)

*Primary Examiner* — Timothy A Musselman
(74) *Attorney, Agent, or Firm* — ALLEN, DYER, DOPPELT, + GILCHRIST, P.A.

(57) ABSTRACT

A surgeon training apparatus includes a cassette, which includes biological tissue repurposed into a form consistent with the anatomical configuration of abdominal hernias, affixed into an anatomically correct silicon framework which replicates the abdominal anatomy. The framework positions the cassette in an anatomically correct position within the abdominal cavity, enabling surgeons to train using a properly positioned representation of the target anatomy, thus requiring the surgeon to properly use surgical tools to (Continued)

correct the pathologic condition caused by the hernia. The cassette is formed by applying biologic tissue to a specially designed "plate," which affixes the tissue block into the anatomic framework, and is adapted for connection to a grounding device so the surgeon can use cautery during the simulated hernia repair. The cassette can be positioned inside a manikin, and can be used to train surgeons to repair human hernias using multiple techniques, including robot assisted and laparoscopic methods.

10 Claims, 9 Drawing Sheets

(51) Int. Cl.
*A61B 34/30* (2016.01)
*A61B 18/14* (2006.01)
*A61G 13/04* (2006.01)
*A61G 13/06* (2006.01)

(56) References Cited

U.S. PATENT DOCUMENTS

| | | |
|---|---|---|
| 2003/0073060 A1 | 4/2003 | Eggert et al. |
| 2010/0209899 A1 | 8/2010 | Park et al. |
| 2012/0148994 A1 | 6/2012 | Hori et al. |
| 2014/0272878 A1 | 9/2014 | Shim et al. |
| 2014/0342334 A1 | 11/2014 | Black et al. |
| 2016/0314711 A1 | 10/2016 | Grubbs |
| 2016/0355676 A1 | 12/2016 | Felsinger et al. |
| 2018/0049858 A1 | 2/2018 | Tao et al. |
| 2018/0240366 A1* | 8/2018 | Felsinger ............... G09B 23/30 |

OTHER PUBLICATIONS

International Preliminary Report on Patentability for Application No. PCT/US2019/021657, dated Sep. 24, 2020, 8 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

ABDOMINAL HERNIA SIMULATION MODEL FOR SURGICAL TRAINING

CROSS REFERENCE TO RELATED APPLICATIONS

This application is a 35 U.S.C. § 371 U.S. national phase entry of International Application No. PCT/US2019/021657 having an international filing date of Mar. 11, 2019, which claims the benefit of U.S. Provisional Application No. 62/641,618, filed Mar. 12, 2018, the contents of each of which is incorporated herein by reference in their entirety.

FIELD OF THE INVENTION

The present invention relates to the field of surgery, where the surgery is performed on a surgical simulator rather than on a live human or animal. The invention further relates to a simulated hernia model for use in surgical simulators.

BACKGROUND OF THE INVENTION

A hernia is a bulge or protrusion of a body tissue or organ through the structure that normally contains it. One way to envision a hernia is to imagine a barrel with a hole in its side, with a balloon blown up inside the barrel. The part of inflated balloon bulging out through the hole is like the tissues of the abdomen bulging through a hernia.

Abdominal herniation is a common herniation. An abdominal hernia is an opening or weakness in the muscular structure of the abdomen wall. The peritoneum (lining of the abdominal cavity) protrudes through the opening, and this defect causes a bulging of the abdominal wall. This bulging is usually more noticeable when the abdominal muscles are tightened, thereby increasing the pressure in the abdomen. Activities, such as weight lifting, coughing, straining and the like increase intra-abdominal pressure and can worsen a hernia.

When the lining protrudes, it can contain intra-abdominal contents such as the intestines and omentum (the layer of fat that covers abdominal organs). Serious complications from a hernia can result from tissues becoming trapped in the hernia—a process called incarceration. Trapped or incarcerated tissues may have their blood supply cut off, leading to damage or death of the tissue.

Several different types of hernia may occur, and frequently coexist, in the groin area. These include indirect, direct, femoral and abdominal wall hernias, which are defined by the location of the opening of the hernia from the abdomen to the groin. An indirect inguinal hernia results from the failure of embryonic closure of the deep inguinal ring after the testicle has passed through it. Like other inguinal hernias, it protrudes through the superficial inguinal ring. This is the most common cause of groin hernia. A direct inguinal hernia enters through a weak point in the fascia of the abdominal wall, and its sac is noted to be medial to the inferior epigastric vessels. A femoral hernia happens when a weakness in the groin muscle allows the intestine to bulge through. An abdominal wall hernia is a protrusion of the intestine through an opening or area of weakness in the abdominal wall. Another type of hernia, called a ventral hernia, occurs in the midline of the abdomen, usually above the navel (umbilicus). Hernias can also occur within the navel (umbilical hernia).

With the exception of internal hernias (within the abdomen), these hernias are commonly recognized as a lump or swelling, and are often associated with pain or discomfort at the site. Internal hernias can be extremely difficult to diagnose until the intestine (bowel) has become trapped and obstructed, because there is usually no external evidence of a lump.

Treatment usually involves surgery, which can be performed using any of a variety of techniques, including open surgery, robot-assisted surgery, and laparoscopic surgical techniques. In the open surgical approach, following appropriate anesthesia and sterilization of the surgical site, an incision is made over the area of the hernia and carried down carefully through the sequential tissue layers. The goal is to separate away all the normal tissue and define the margins of the hole or weakness. Once this has been achieved, the hole is then closed, usually by some combination of suture and a plastic mesh. When a repair is done by suture alone, the edges of the defect are pulled together, much like sewing a hole together in a piece of cloth. One of the possible complications of this approach is that it can put excessive strain on the surrounding tissues through which the sutures are passed. Over time, with normal bodily exertion, this strain can lead to the tearing of these stressed tissues and the formation of another hernia. The frequency of such recurrent hernias, especially in the groin region, has led to the development of many different methods of suturing the deep tissue layers in an attempt to provide better results.

In order to provide a secure repair and avoid the stress on the adjacent tissue caused by pulling the hole closed, an alternative technique was developed which bridges the hole or weakness with a piece of plastic-like mesh or screen material. The mesh is a permanent material and, when sewn to the margins of the defect, it allows the body's normal healing process to incorporate it into the local structures. Hernia repair with mesh has proved to be a very effective means of repair.

PTFE (polytetrafluoroethylene) and polypropylene meshes are the types most commonly used for hernia repair. PTFE is softer and more pliable than polypropylene mesh, and is associated with reduced incidence of adhesions and bowel erosion. However, it has much smaller pores, which could harbor bacteria. It therefore carries increased risk of infection and is not recommended for use in an infected field, as may be present during emergent procedures. It is also subject to shrinkage and is unsupportive of tissue ingrowth. Biosynthetic materials, such as those made from human or porcine collagen, are increasingly being used in other forms of hernia repair and offer another alternative, but lack of long-term data means their impact upon re-herniation rate is currently unclear.

After the hernia repair is completed, the overlying tissues and skin are surgically closed, usually with absorbable sutures.

More and more of hernia repairs are now being done using laparoscopic techniques. In these techniques, a surgeon makes small incisions on the abdominal wall to start the surgery. The layer of the abdomen just below the muscles is inflated with carbon dioxide, and the laparoscope and surgical instruments are inserted through the incisions. With the help of a monitor, the surgeon pushes the herniated intestine into place and then uses a surgical mesh to repair the hernia opening.

Laparoscopic inguinal hernia repair offers certain advantages over open surgical repair. For example, laparoscopic surgery offers a quicker recovery, a reduced risk of infection, and reduced recurrence of hernias. An added advantage is that laparoscopic inguinal hernia repair may be easier an open surgical techniques. Further, there is occasionally a second hernia found at the opposite side during the operation, and the surgeon can quickly identify and repair the second hernia when laparoscopic surgery is performed.

It would be advantageous to have the ability to simulate hernia surgeries, in order for surgeons to be able to practice surgeries on a simulated model rather than learning on a live patient. However, on information and belief, there are currently no usable animal anatomically correct portions of tissue that can be used to train surgeons because there are no animal anatomically similar configurations occurring in nature. This contrasts with the porcine heart and lungs which are very similar in size and structure to human anatomy, i.e., simulations using porcine heart and lungs can be accomplished using the intact organ because of the anatomic similarities.

The present invention relates to a model for use in simulated hernia surgeries.

SUMMARY OF THE INVENTION

In one embodiment, the present invention relates to a model for use in simulated hernia surgeries.

The hernia simulation model comprises a "cassette," where the focal point of the simulation and the structural anatomy of the hernia and closely surrounding tissue are contained in the "cassette." The cassette can be affixed into an anatomically correct silicon framework in the abdominal cavity of a mannequin, which replicates the abdominal anatomy, that is, is a simulated abdominal cavity.

The framework positions the cassette in an anatomically correct position within a simulated abdominal cavity. This enable the surgeon to train using a representation of the target anatomy positioned into anatomically correct manner, which necessitates proper use of surgical tools the surgeon will use to correct the pathologic condition caused by the (simulated) hernia.

The cassette is created by applying biologic tissue, for example, a suitably-sized section of pork belly covered with a sheet of bovine pericardium, to a specially designed "plate," which plate is used to affix a tissue block into the anatomic framework. This tissue on the plate is adapted for connection to a grounding device. By grounding the tissue, the surgeon can use cautery during the hernia repair. This feature is included to allow the surgeon to train using this important surgical tool during the simulated hernia repair process.

The "plate" is also adapted to enable rapid changes of the cassette, which can facilitate surgical training of multiple surgeons. The plates can be removed and replaced in a relatively rapid manner, so that multiple duplicative procedures can be done. In this manner, a single surgeon can practice a simulated hernia operation multiple time, and/or multiple surgeons can practice a simulated hernia operation.

The hernia tissue block is constructed using muscle and fat-containing tissue that is cut and constructed in a manner to mimic abdominal wall tissue representative of the specific type of hernia being simulated. Representative hernia types which can be represented include, but are not limited to, indirect, direct, femoral, ventral, umbilical, and abdominal wall hernias.

The vascular and other structures such as nerves and ligamentous structures are represented in anatomically correct positions using various inanimate and/or biologic structures which are affixed to the tissue block.

The hernia cavity in the tissue block is created in a fashion that represents the size and shape of the pathologic condition.

In one embodiment, a covering for the tissue block, which includes the tissue of the simulated hernia sac, is adhered to the tissue block in a manner which replicates the qualities of the inner lining of the abdominal cavity. The glue is formulated to attach the various tissues in a way that replicates the natural adherence of these tissues found in the replicated human anatomy.

Any suitable glue can be used to adhere the covering to the tissue block, and cyanoacrylate glues are a representative type of glue which can be used.

The completed "cassette comprises the constructed tissue block and the plate as a single unit.

In one embodiment, the completed "cassette" is stored in a storage solution which is then vacuum sealed for storage. The storage solution, which in one aspect of this embodiment, comprises one or more of methanol, ethanol, isopropyl alcohol, preserves the tissue until use.

To prepare the stored cassette for use in simulated surgery, the cassette is first removed from the vacuum sealed bag, and, optionally, a salt solution in a hydrogel is applied to the tissue, ideally as a thin layer, to replicate the moisture consistency of human tissue. Ideally, the salt solution is applied just prior to use in order to preserve the proper moisture content of the tissue, and its electrical conductivity. The solution, in addition to the grounding of the tissue on the plate, allows the surgeon to practice cautery on the tissue.

One example of a suitable salt solution is a solution of salt, such as sodium chloride or potassium chloride, in a hydrogel formulation, such as KY jelly, polyethylene glycol, and the like. The use of hydrogels can be preferred over ordinary salt solutions because of the added viscosity. The added viscosity tends to add a more realistic "feel" to the tissue.

In another embodiment, the model is placed in a simulated "patient" mannequin or other simulated "patient," which is then used during simulated surgical procedures. In one aspect of this embodiment, the mannequin is carried by a mannequin support structure, and has a body cavity corresponding to an abdomen.

In yet another embodiment, the hernia model, and, optionally, a mannequin or other simulated "patient" including the hernia model, is used in open surgery, laparoscopic surgery, which in one embodiment, is robotic surgery.

Particularly where the hernia model is intended for use in simulated open surgery, the model may include a layer of skin, optionally with an underlying layer of fat. In this manner, a surgeon can practice cutting into the "patient," then inserting the mesh, and then suturing the mesh in place.

Whether used for simulated open surgery or simulated laparoscopic surgery, the model may optionally also include a loop of intestine sticking through a hole in the simulated abdomen, to simulate "incarcerated" tissue. In the simulated surgery, the surgeon would push this incarcerated tissue back through the hole, then install the mesh, and then stick the mesh to the surrounding abdominal tissue. As pushing the incarcerated tissue through the hole does not require the same level of training as the remainder of the hernia operation, the presence of incarcerated tissue is optional.

The present invention will be better understood with reference to the following Detailed Description.

DETAILED DESCRIPTION

Figure 1:
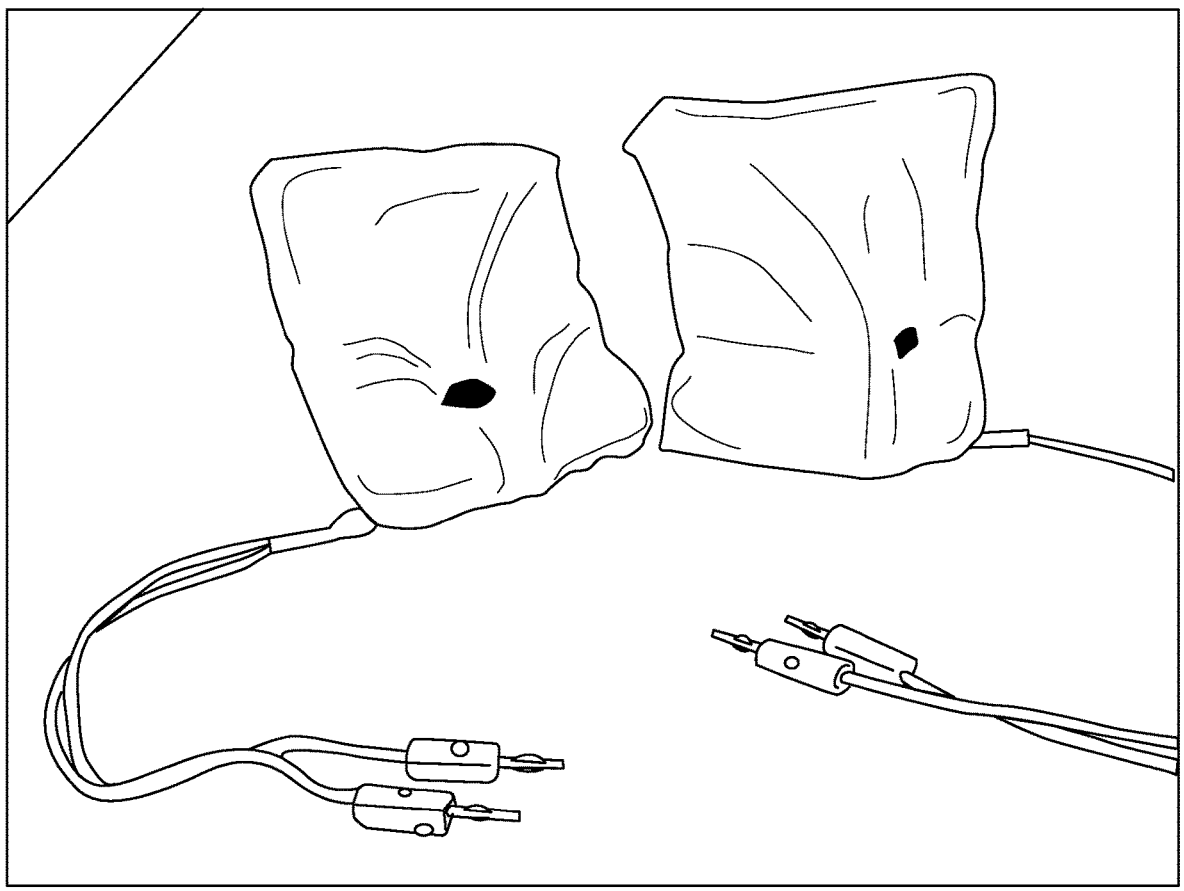
FIG. 1 is a front view of tissue blocks that include a hole simulating a hernia, as well as grounding wires.

Models for use in simulated hernia surgeries, and simulated surgeries using such models, are disclosed. The present invention will be better understood with reference to the following definitions.

Definitions

As used herein, a "cassette" is a tray, such as a plastic tray, which includes tissue simulating a hernia, attached to a plate and adapted for being grounded. The cassette can be placed precisely in an abdominal mannequin, and the grounding connection, which can come out of the "abdominal" wall, allows for the cassette to be grounded, which in turn allows for the surgeon to use electrocautery.

As used herein, a hernia is a bulge or protrusion of a body tissue or organ through the structure that normally contains it. Representative hernia types which can be represented include, but are not limited to, indirect, direct, femoral, ventral, umbilical, and abdominal wall hernias A. Surgical Techniques Used to Repair Hernias A hernia is the protrusion of tissue through a weak spot in the surrounding wall of the cavity that normally contains it. Because of this opening of the wall, an organ or a part of an organ squeezes through and reaches another region of the body, forming kind of protruding 'sac' (hernia sac).

Although several surgical approaches to hernia repair have been developed, all share some basic common principles:

Inversion/Removal of the Hernia Sac

The protruding tissue is returned to where it belongs, by dissecting the surrounding tissues, locating the hernia sac and its contents, and either inverting the hernia sac (i.e., pushing or pulling it back) or opening and removing it (i.e., a herniotomy).

Closure/Reinforcement of the Opening which Resulted in the Hernia

Hernias result from a weak spot, typically an opening in the abdomen, through which the hernia came out. This weak spot is typically closed and reinforced, so that it remains closed, by either stitching the defect or using an implant/patch to fix the opening as a patch.

These steps can be performed using an open surgical approach or a laparoscopic approach, which can be a robotic surgical approach.

Differences Between Open, Laparoscopic, and Mini-Open Techniques

During an open surgical approach, a single incision is made, whereas in a laparoscopic approach, multiple, very small incisions are made. In either case, the defect can be closed using just stitching (herniorrhaphy), or using a mesh implant (hernioplasty). Stitching is done under tension, whereas the mesh implant is done in a tension-free manner.

Where a mesh implant is used, it can be placed above the muscle layers (onlay), among the muscle layers (inlay), or below the muscle layers (sublay, preperitoneal). Placing the mesh below the muscle layers seems to provide the best bio-mechanics, while placing the mesh above the muscle seems to provide the worst bio-mechanics.

Another approach is known as the "mini-open" hernia repair, and is used for both inguinal and femoral hernia repairs. This type of procedure can be performed using local anesthesia, and is different than a laparoscopic hernia repair or a traditional open hernia repair. Mini-open hernioplasty, with preperitoneal mesh, differs from a traditional open approach in that the mesh implant is placed in the deepest layer of the abdominal wall, and not between the muscles, as in the conventional open methods. This approach can purportedly provide better bio-mechanics and increased stability for the hernia repair.

Yet another approach is referred to as the "Shouldice Method." In this approach, the surgeon can prevent the hernia from continuing to push out from the abdominal cavity without implanting plastic mesh. This procedure involves repositioning nearby muscles so that they themselves block the hernia, under no significant tension, and without implanting the plastic mesh.

As discussed below, when a surgeon practices the open or mini-open approaches, the hernia model ("cassette") may be slightly different than when a laparoscopic approach is practiced.

B. Hernia Model ("Cassette")

The hernia model, or "cassette" has several parts. These include the biological tissue which mimics a patient's abdomen when a hernia operation is being simulated, the plate to which the tissue is attached, the grounding device, the vacuum sealed bag in which the cassette is stored, and the salt/hydrogel solution applied to the tissue so as to increase the conductivity of the tissue. As discussed above, the grounded plate and the applied solution allow the surgeon to practice electrosurgical cautery, which stops and/or prevents bleeding during and after surgery.

Biological Tissue

The abdominal wall has several layers, including skin, subcutaneous tissue, subcutaneous fat, muscle, and peritoneum (the membrane that forms the lining of the abdominal cavity, the deepest layer of the abdominal wall just above the intestines). One or more of these types of tissues are present in the cassette.

The hernia tissue block is typically constructed using muscle and fat-containing tissue that is cut and constructed in a manner to represent the abdominal wall tissue that is representative of the specific hernia being simulated.

The vascular and other structures such as nerves and ligamentous structures are represented in anatomically correct positions, using various inanimate and biologic structures which are affixed to the tissue block.

The hernia cavity in the tissue block is created in a fashion that represents the size and shape of the pathologic condition, and those of skill in the art, such as surgeons, understand what an appropriate size and shape is, depending on the type of hernia being simulated.

The covering of the tissue block which includes the tissue of the hernia sac can be applied to the tissue block using glue. Ideally, the glue replicates the qualities of the inner lining of the abdominal cavity. In one embodiment, the glue is a cyanoacrylate glue. The glue is ideally formulated to attach the various tissues in a way that replicates the natural adherence of these tissues found in the replicated human anatomy.

When the surgery being simulated is an open (or mini-open) surgery, it is useful for the biological tissue used in the cassette to include a layer of skin. In this manner, the surgeon can practice the initial incision.

It has been determined that portions of porcine abdominal wall (pork belly), appropriately sized to fit in the cassette, for example, with a size of approximately 6 inches by 6 inches, mimic the human abdomen for purposes of practicing hernia repair. That is, the porcine abdominal wall includes both muscle and fat, and thus mimics the portion of the human body in which the surgeon is to practice many types of hernia repair.

To simulate a hernia, the muscle layer in the abdomen includes an opening, which is typically between about 2 in length with a tunnel about 8 cm in length which simulates the inguinal canal. It is this opening which is either closed using stitches, or by applying a mesh to the opening, which is then sutured in place.

In some embodiments, a loop of intestine can be used to simulate incarcerated tissue. In these embodiments, the loop of intestine protrudes between about 1 and about 4 cm from the opening in the abdomen, and the amount of intestine lying underneath the "abdomen" can vary. All that is required is that there be sufficient intestine above the opening in the abdomen for the surgeon to be able to practice pushing the intestine back through the opening.

The intestine can be filled with simulated intestinal contents (such as simulated intestinal fluid), so that if the surgeon inadvertently nicks the intestine, the contents would leak out and provide a visual cue to the surgeon. Particularly for use in simulated open or mini-open surgery, the fluid may also contain an odorant, such as butyric acid, to provide an olfactory cue to the surgeon in the event the surgeon nicks the intestine.

Since there is less of a need to practice pushing the intestine through the opening as there is to practice installing the mesh, the intestine is an optional component. However, the presence of intestine protruding through the opening does provide a more realistic experience for the surgeon, allowing the surgeon to deal with incarcerated tissue.

In some embodiments, the portion of the intestine which is incarcerated can be treated so as to appear to be infected, which would cue the surgeon to remove that portion of the intestine during the hernia repair. The ability to train surgeons to address this type of potential complication in hernia surgeries can be particularly advantageous.

The tissue used in the cassette is ideally not cadaverous tissue, but rather, animal tissue, such as porcine tissue, although other types of animal tissue can be used.

Silicon Framework

The hernia simulation model uses the cassette concept, where the focal point of the simulation and the structural anatomy of the hernia and closely surrounding tissue are contained in the "cassette." The cassette is affixed, and, ideally, releasably affixed, into an anatomically correct silicone framework which replicates the abdominal anatomy. The framework positions the cassette in an anatomically correct position within the simulated abdominal cavity. The term "releasably affixed" means that cassettes can be installed, and removed, from the abdominal cavity in a manner which facilitates preparing a number of cassettes being used on the same mannequin to train one surgeon multiple times, or multiple surgeons one or multiple times.

The silicone framework can be prepared using silicone casting, and dyed to appear more natural using a dyeing process. Anatomical illustrations can be used in the casting step to provide an accurate model. Those of skill in the art of mannequin manufacture understand to how to build a mannequin with an anatomically correct abdominal cavity. This enables the surgeon to train using a representation of the target anatomy positioned into anatomically correct anatomy that necessitates proper use of the tools the surgeon will use to correct the pathologic condition caused by the hernia.

The Cassette

The completed cassette includes the entire constructed tissue block and a plate.

The cassette is created by applying the biologic tissue to a specially designed "plate" that is used to affix the tissue block into the anatomic framework. This plate is adapted to allow for attachment of a grounding device which electrically grounds the tissue. When grounded, the plate enables the surgeon to use electrocautery during the simulated hernia repair.

The grounding capacity of the model can also be changed out quickly which facilitates the learning process. Each cassette has built into it a grounding device which can be connected to the grounding wire that leads to the electrocautery unit.

Storage of the Cassettes

Once the "cassettes" are completed, they can be stored, preferably under vacuum, such as in a vacuum-sealed bag. The cassettes are ideally stored at a relatively low temperature, for example, 4 degrees Celsius, in an alcoholic solution, for example, 10% ethanol.

In this manner, the tissues typically remain fresh for at least 1 month. If higher concentrations of alcohol, such as 40% ethanol, are used, one can preserve the tissues for over a year, and, ideally, up to 18 months, and can perform as well as freshly-harvested tissues.

Preparation of the Cassette for Simulated Surgery

When the cassette is prepared for use, it is removed from the vacuum sealed bag, and a (preferably thin) layer of a salt solution in a hydrogel is applied to the tissue prior to use, ideally within one hour of use in simulated surgical procedures.

The salt/hydrogel solution replicates the moisture consistency of human tissue in order to preserve the proper moisture content of the tissue and its electrical conductivity. Electrical conductivity can be important when a surgeon practices electrocautery, since the tissue will need to conduct electricity in order to be cauterized.

One example of a suitable salt solution is a solution of salt, such as sodium chloride or potassium chloride, in a hydrogel formulation, such as KY jelly, polyethylene glycol, and the like. The use of hydrogels can be preferred over ordinary salt solutions because of the added viscosity. The added viscosity tends to add a more realistic "feel" to the tissue.

Grounding Device

The tissue on the plate is attached to a grounding device, so as to ground the cassette. This facilitates the use of electrocautery during simulated surgery. Representative grounding devices include grounding pads, such as those sold by Xodus Medical, Halyard Health, Wallach Surgical Devices, and DeRoyal, dispersive electrodes, such as those sold by Conmed, and split return electrodes, such as those sold by Bovie Medical Corp.

C. Open Surgery and Laparoscopic Surgery, Including Robotic Surgery

The cassette can be included in a carrier/container to simulate the view a surgeon would see when performing surgery. This view may simply include draping over the cassette to be operated on, at the height appropriate for the surgeon to perform the surgery. However, in some embodiments, the cassette is included in a mannequin, and/or are provided along with photographs representative of what would be seen in an actual human undergoing this surgical procedure, so as to provide a more realistic surgical experience. The mannequin can be draped to expose the relevant surgical sites.

If a mannequin is used, the mannequin can be tilted or moved using an actuator, if desired.

A surgery system for use in simulated laparoscopic surgery simulates a patient undergoing laparoscopic surgery. It includes an operating table, and, ideally, a mannequin which includes the hernia cassette. The mannequin is mounted on the operating table. If desired, the mannequin can include simulated heart and/or lungs, which can be animated, to further simulate a live patient. Where the laparoscopic surgery being simulated is robotic surgery, components of a robotic surgical system can be present.

In some embodiments, a blood perfusion device can be coupled to one or more blood vessels in the tissue, which, in a preferred embodiment, does not include human cadaver tissue, and ideally includes porcine, sheep, goat, or canine tissue.

The major types of hernia repair surgery have been discussed elsewhere, but are summarized below with respect to how one can simulate such surgery using the cassettes described herein.

Hernias are typically repaired using a synthetic mesh either with open surgery or laparoscopic procedures. The surgeon can practice installing the mesh and suturing it to the abdomen using the cassettes described herein, and the use of proper grounding and/or the salt/hydrogel solution on the tissue also allows the surgeon to practice electrocautery.

For open or mini-open surgery, an incision would be made over the portion of the "abdomen" in the cassette where the hernia is located. The surgeon would then, if the cassette includes a portion of intestine protruding through the "abdomen," push the intestine through the opening in the abdominal wall, and either stitch the opening shut, or install mesh. The "patient" could then be "closed."

Laparoscopic surgery can be performed robotically, or using non-robotic systems. In those embodiments where the laparoscopic surgery is performed robotically, the surgeon uses robotic surgical equipment rather than non-robotic laparoscopic equipment.

For laparoscopic surgery, a series of small incisions, typically three incisions, can be placed in the "abdomen." One incision is to accommodate the laparoscope, and the other two are to accommodate specific surgical instruments used in a laparoscopic surgery, such as forceps, scissors, probes, dissectors, hooks, retractors and the like.

The most common laparoscopic techniques for inguinal hernia repair are transabdominal preperitoneal (TAPP) repair and totally extraperitoneal (TEP) repair.

In TAPP the surgeon goes into the peritoneal cavity and places a mesh through a peritoneal incision over possible hernia sites. TEP is different in that the peritoneal cavity is not entered and mesh is used to seal the hernia from outside the peritoneum (the thin membrane covering the organs in the abdomen). This approach is considered to be more difficult than TAPP, but may have fewer complications.

In laparoscopic surgery, the "abdomen" is inflated with carbon dioxide, which gives the surgeon a better view of the "patient's" organs. The surgeon then makes a few small incisions (cuts) near the simulated hernia, and inserts a thin tube with a tiny camera on the end (i.e., a laparoscope). The surgeon uses images from the laparoscope as a guide to repair the hernia, for example, with mesh.

Surgical instruments are inserted through the other small openings, and used to perform various steps of the operation, including freeing the incarcerated intestine, placing the mesh, suturing the mesh to a desired portion of the abdomen, using electrocautery as needed, for example, to free the incarcerated tissue from the peritoneum, or to stop bleeds, and closing the patient.

Since the cassettes can quickly be installed and changed out, the systems described herein allow for one surgeon to practice hernia repair multiple times, and/or for multiple surgeons to practice hernia repair on the same device.

Accordingly, using the systems described herein, including the cassettes, and the mannequins into which the cassettes are installed, surgeons can adequately simulate hernia repair surgery. The present invention will be better understood with reference to the following non-limiting examples.

Example 1: Representative Cassette

Aspects of a representative cassette is shown in FIGS. 1, 2A-B, 3A-C, 4, 5 and 6.

FIG. 1 is a photograph showing tissue blocks that include a hole simulating a hernia. Grounding wires are in place, which allow the tissue to be grounded, thus allowing the surgeon to practice electrocautery. The tissue blocks are applied to the plate shown in FIGS. 2A and 2B.

Figure 2A:
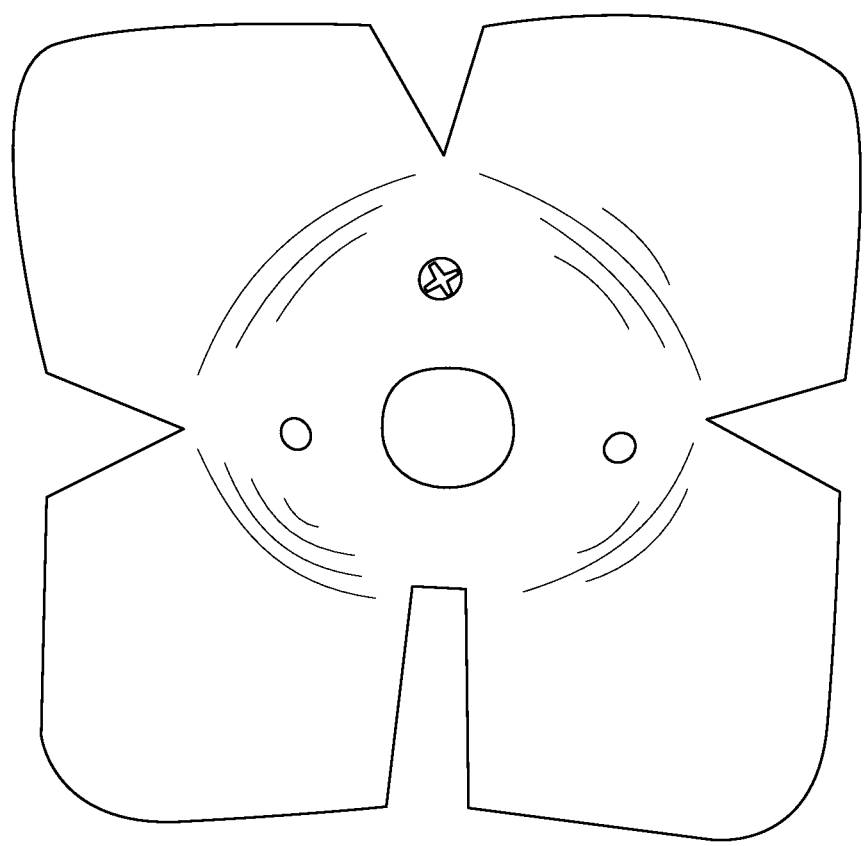
FIG. 2A is a top side view of a representative plate used in the completed cassette, used to simulate a ventral hernia, showing a screw head, which corresponds to a pin (attached to the plate, in this embodiment, via the screw), shown in FIG. 2B.

FIG. 2A is a photograph of the top side of a representative plate used in the completed cassette in connection with a simulated ventral hernia. The tissue blocks are adhered to the top side of the plates. A screw head is visible, and the screw head corresponds to a pin (attached to the plate, in this embodiment, via the screw), shown in FIG. 2B. Note that the block includes additional holes, which allow additional pins to be attached. These additional pins can correspond to holes in the abdomen of different mannequin types, thus allowing the cassette to be adaptable for use with multiple mannequin types. Where the plate is angled, and the pins are therefore not parallel to each other, the points of attachment can function like a dovetail joint, making the attachment more rigid than when the pins are parallel to each other. In place of pins, other means for attaching the plate to the abdominal cavity can be used, if desired. Those of skill in the art understand how to releasably attach a plate to a cavity sized to receive the plate, including using Velcro and other releasable attachments.

Figure 2B:
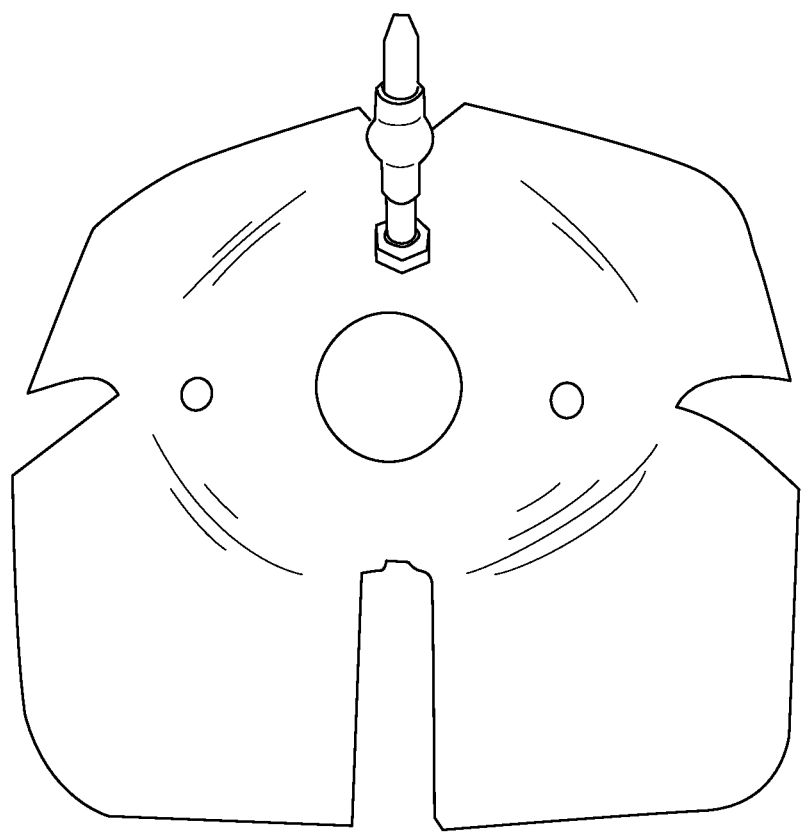
FIG. 2B is a bottom side view of a plate used in the completed cassette, used to simulate a ventral hernia, which includes a pin which can be used to make a physical connection with a corresponding hole in the abdominal cavity of a mannequin.

FIG. 2B is a photograph of the bottom side of a plate used in the completed cassette in connection with a simulated ventral hernia. A pin is shown, and the pin is used to make a physical connection with a hole in the abdominal cavity on a mannequin. The pin/hole connection allows the cassette to be positioned in the correct anatomical position on the mannequin. Installing the cassette in the correct anatomical position on the mannequin assists the surgeon in performing a simulated hernia operation which most closely simulates what would be observed on an actual live human patient.

As discussed above, the tissue block is attached to the plate, and stored, refrigerated, in a solution. The completed cassette is stored, along with this solution, in a vacuum bag. FIG. 3 is a photograph of a completed cassette, stored in a vacuum bag for later use.

In use, the completed cassette is removed from the vacuum bag, and, optionally but preferably, a thin film of a salt/hydrogel solution is applied to the tissue. The cassette is then installed into the abdominal cavity of a mannequin.

Figure 3A:
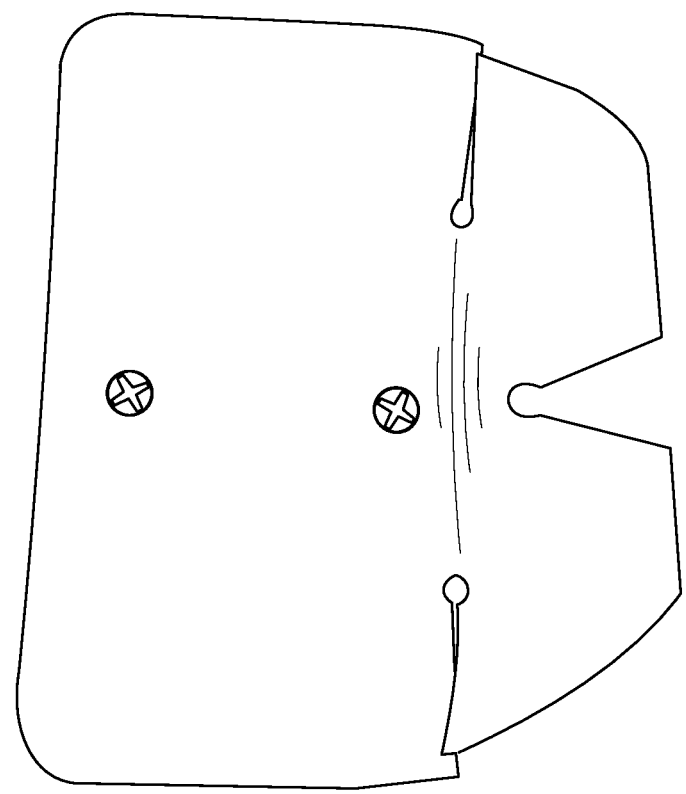
FIG. 3A is a top side view of a representative plate used in the completed cassette, used to simulate an inguinal hernia, showing a screw head, which corresponds to a pin (attached to the plate, in this embodiment, via the screw), shown in FIG. 3B.
Figure 3B:
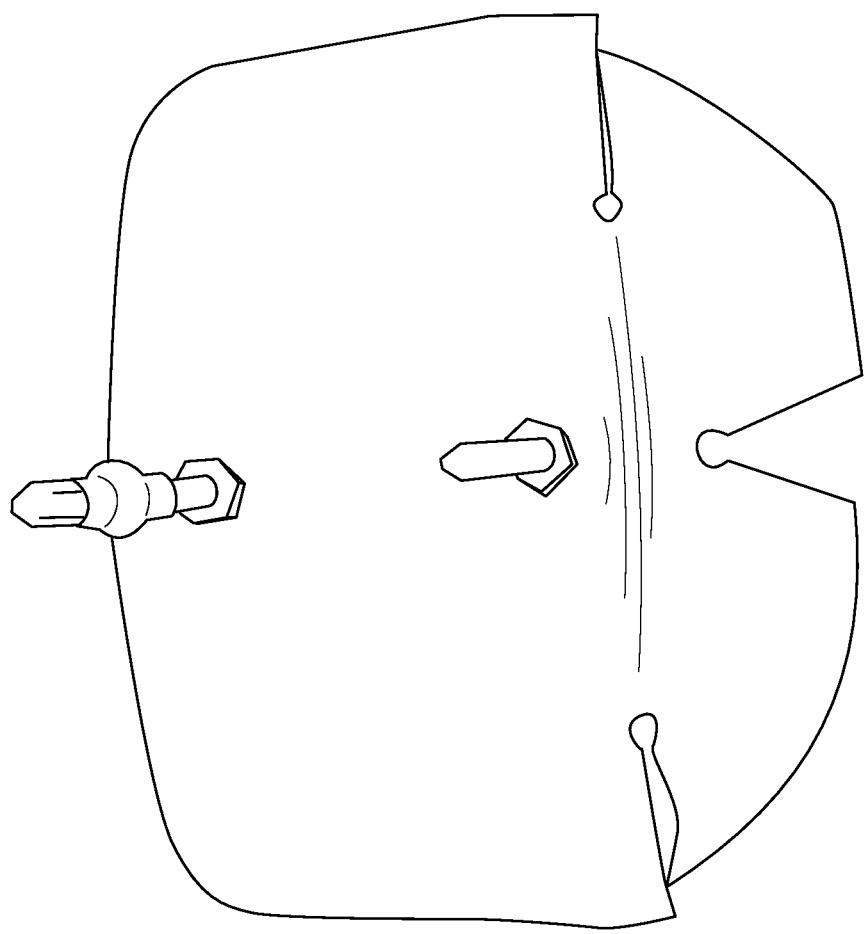
FIG. 3B is a bottom side view of a plate used in the completed cassette, used to simulate an inguinal hernia, which includes a pin which can be used to make a physical connection with a corresponding hole in the abdominal cavity of a mannequin.
Figure 3C:
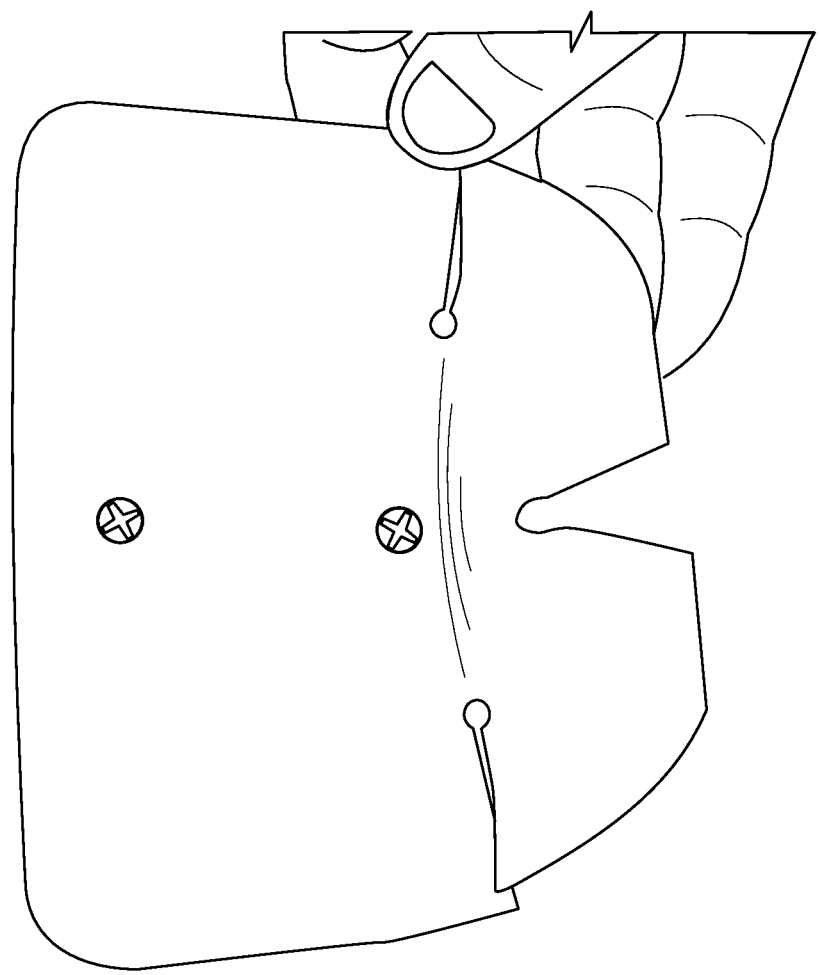
FIG. 3C is a top side view of the plate shown in FIG. 3A, held in a user's hand, to show a representative size of the plate.
Figure 4:
FIG. 4 is a photograph of a representative completed cassette, stored in a vacuum bag for later use.

FIGS. 3A and 3B are photographs of plates used to prepare cassettes to mimic inguinal hernias. FIG. 3C is a photograph of the plate, held in a user's hand, to show a representative size of the plate.

Figure 5:
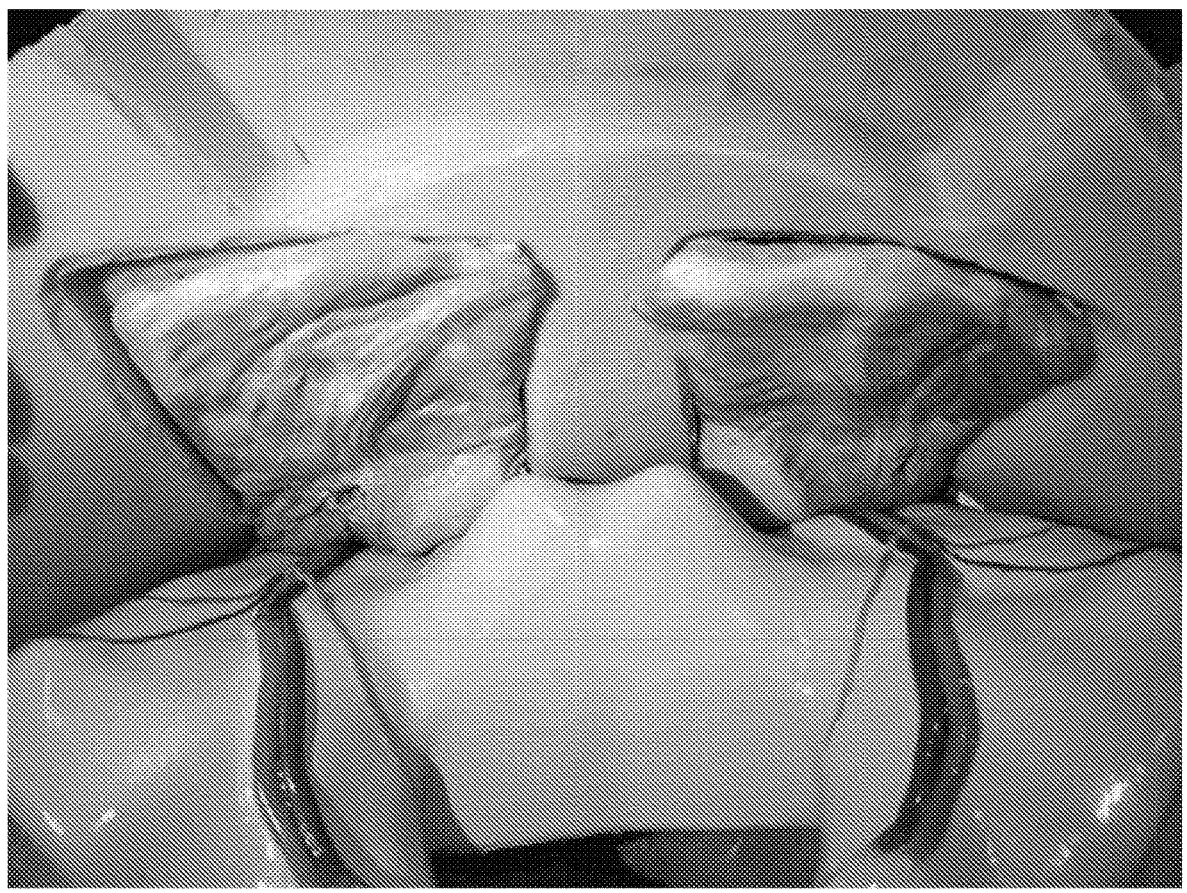
FIG. 5 is a photograph of a representative cassette, which includes a hole which simulates a hernia, and where the cassette is installed in the abdominal cavity of a mannequin.

FIG. 5 is a photograph of a representative cassette, installed in the abdominal cavity in a mannequin. A hole, which simulates a hernia, is visible.

Figure 6:
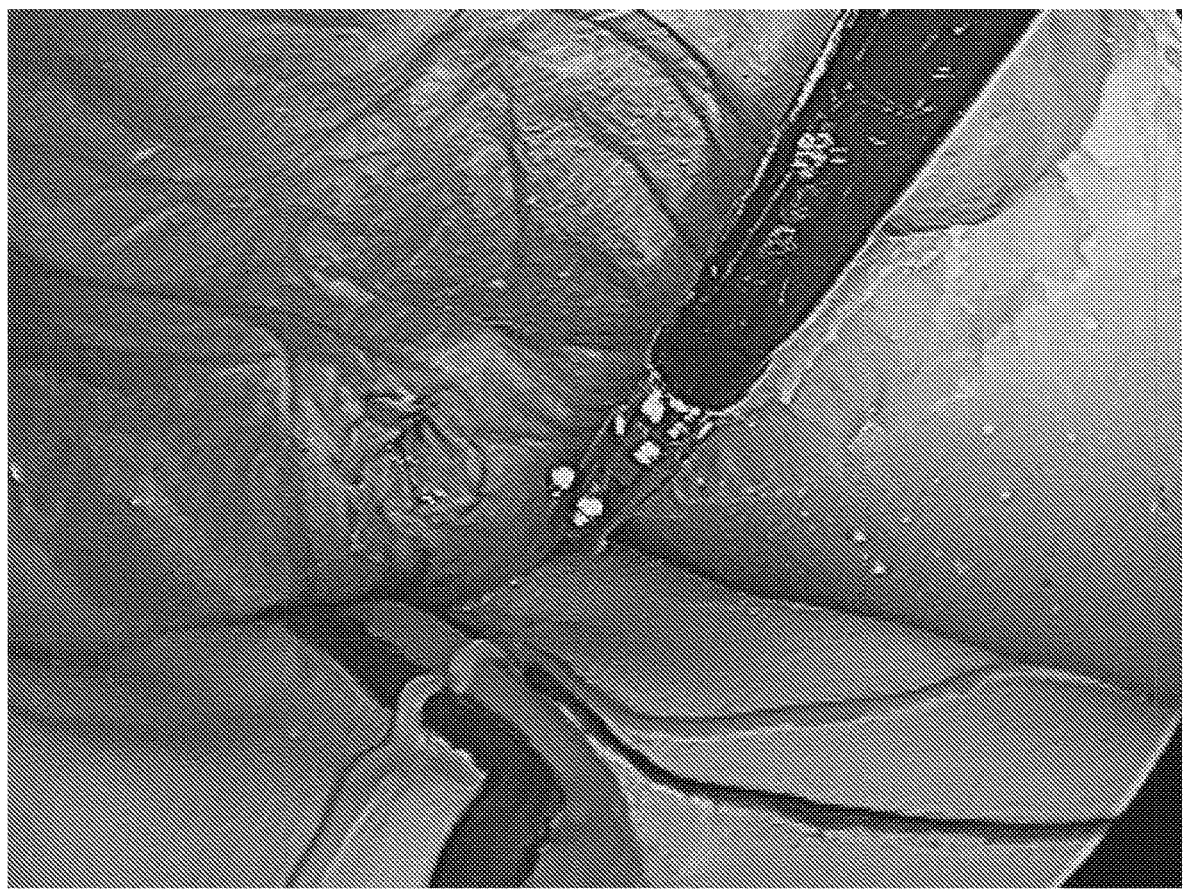
FIG. 6 is a photograph of a representative cassette installed in the abdominal cavity of a mannequin, where a laparoscopic instrument is in place, ready for use in a simulated hernia operation. Although the cassette includes a plate and a tissue block, only the tissue block is visible once the cassette is installed in the abdominal cavity. The tissue block includes a hole, which simulates a hernia. A portion of the mannequin which includes a silicone representation of the abdominal wall is shown to the right of the tissue block.

FIG. 6 is a photograph of a representative cassette in place in an abdominal cavity in a mannequin, where a laparoscopic instrument is in place, ready for use in a simulated hernia operation. The tissue block includes a hole, which simulates a hernia. The tissue block is present on a block (shown in FIGS. 2A and 2B, though not visible in this picture). A portion of the mannequin which includes a silicone representation of the abdominal wall is shown to the right of the tissue block.

The individual components of the cassette, a completed cassette stored for later use, and a cassette installed into an abdominal cavity for use in simulated surgery, have been shown and described in these figures. A surgeon can readily practice simulated hernia surgeries using this cassette.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

The invention claimed is:

1. A cassette comprising:
a section of pork belly tissue mimicking a hernia, and a plate to which the section of pork belly tissue is adhered,
wherein the plate is adapted to be connected to a grounding device to electrically ground the section of pork belly tissue to facilitate electrocautery, and to affix the section of pork belly tissue into a simulated anatomic framework that mirrors the human abdomen.

2. The cassette of claim 1, wherein the simulated anatomic framework is a silicone model of the abdominal cavity.

3. The cassette of claim 1, wherein the cassette is adapted for insertion into the simulated abdominal cavity of a mannequin.

4. The cassette of claim 1, further comprising a film of a salt/hydrogel solution overlying all or part of the section of pork belly tissue.

5. A surgeon training apparatus comprising:
a) a mannequin, and
b) the cassette of claim 1 inserted into the mannequin.

6. The surgeon training apparatus of claim 5, further comprising an operating table, over which the mannequin is placed.

7. The surgeon training apparatus of claim 6, wherein an actuator is configured to raise/lower and tilt the mannequin.

8. The surgeon training apparatus of claim 6, further comprising a robotic surgery station adjacent to the operating table and comprising at least one surgical tool.

9. A method for training a surgeon, comprising:
a) providing a cassette of claim 1, and a mannequin into which the cassette is installed,
b) having a surgeon practice hernia repair on the cassette.

10. The method of claim 9, wherein the surgery is robotic laparoscopic surgery, further comprising manipulating at least one surgical tool at a robotic surgery station during surgical training.

* * * * *